(12) United States Patent
Ota

(10) Patent No.: US 10,583,469 B2
(45) Date of Patent: Mar. 10, 2020

(54) NOZZLE WASHING APPARATUS, DISPENSING APPARATUS, AND METHOD FOR WASHING NOZZLE

(71) Applicant: ARKRAY, Inc., Kyoto-shi, Kyoto (JP)

(72) Inventor: Shinichi Ota, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 0 days.

(21) Appl. No.: 16/017,750

(22) Filed: Jun. 25, 2018

(65) Prior Publication Data

US 2018/0369882 A1 Dec. 27, 2018

(30) Foreign Application Priority Data

Jun. 27, 2017 (JP) .................................. 2017-124984

(51) Int. Cl.
| | | |
|---|---|---|
| *B08B 9/032* | (2006.01) | |
| *G01N 35/10* | (2006.01) | |
| *B08B 3/04* | (2006.01) | |
| *G01N 33/493* | (2006.01) | |
| *G01F 23/26* | (2006.01) | |

(52) U.S. Cl.
CPC ............. *B08B 9/032* (2013.01); *B08B 3/04* (2013.01); *G01N 33/493* (2013.01); *G01N 35/1004* (2013.01); *B01L 2200/141* (2013.01); *G01F 23/263* (2013.01); *G01N 2035/1025* (2013.01)

(58) Field of Classification Search
None
See application file for complete search history.

(56) References Cited

U.S. PATENT DOCUMENTS

2015/0346231 A1* 12/2015 Mori .................. G01N 35/1004
422/67

FOREIGN PATENT DOCUMENTS

| JP | 2000-321270 A | | 11/2000 |
|---|---|---|---|
| JP | 2002-162403 | * | 6/2002 |

OTHER PUBLICATIONS

Google Patents Translation of JP2002-162403 by Suzuki et al., published Jun. 7, 2002.*
The extended European search report issued by the European Patent Office dated Nov. 6, 2018, which corresponds to EP18179567.5-1001 and is related to U.S. Appl. No. 16/017,750.

* cited by examiner

*Primary Examiner* — Mikhail Kornakov
*Assistant Examiner* — Ryan L. Coleman
(74) *Attorney, Agent, or Firm* — Studebaker & Brackett PC

(57) ABSTRACT

The amount of consumption of a washing solution for a nozzle and the required time for washing are reduced. A nozzle washing apparatus usable for collection of a specimen comprises a washing tank which accommodates a nozzle, a first discharge port which discharges a washing solution supplied into the washing tank from an upper portion of the washing tank, a second discharge port which discharges the washing solution supplied into the washing tank from a position lower than the first discharge port of the washing tank, a detector which detects a range of contact of an outer wall of the nozzle with the specimen, and a controller which discharges the washing solution supplied into the washing tank from one of the first discharge port and the second discharge port on the basis of a detection result obtained by the detector.

3 Claims, 6 Drawing Sheets

NOZZLE WASHING APPARATUS, DISPENSING APPARATUS, AND METHOD FOR WASHING NOZZLE

CROSS REFERENCE TO RELATED APPLICATIONS

This application claims priority to Japanese Patent Application No. 2017-124984 filed on Jun. 27, 2017 the entire contents of which are incorporated by reference herein.

TECHNICAL FIELD

The present disclosure relates to a nozzle washing apparatus, a dispensing apparatus provided with the nozzle washing apparatus, and a method for washing a nozzle.

BACKGROUND ART

An analysis apparatus, which has a nozzle for collecting a specimen, is hitherto known (see, for example, Patent Literature 1). The specimen is brought in contact with the interior and the outer wall of the nozzle on account of the collection of the specimen to cause the contamination. Therefore, the interior and the outer wall of the nozzle are washed after the collection of the specimen. For example, in the case of an inspection apparatus described in Patent Literature 1, the entire nozzle is accommodated in a washing tank, and a washing solution is emitted from the nozzle into the washing tank to wash the interior. Further, the washing solution, which is emitted into the washing tank, is sucked from an upper portion of the washing tank by means of a negative pressure, and thus the outer wall of the nozzle is washed.

PRIOR ART LITERATURE

Patent Literature

Patent Literature 1: Japanese Patent Application Laid-Open No. 2000-321270

SUMMARY

Technical Problem

However, in the case of the conventional technique, the washing solution, which is emitted from the nozzle into the washing tank, is discharged from a discharge port provided at the upper portion of the washing tank by means of the negative pressure.

On the other hand, when the specimen is collected, a case arises such that the specimen adheres to the forward end portion of the outer wall of the nozzle but the specimen does not adhere to the upper portion of the outer wall of the nozzle, depending on a situation of the specimen and/or a method for collecting the specimen, for example, a case in which the amount of the specimen is small, or in which the specimen is collected from the vicinity of the liquid surface of the specimen. However, on account of the structure of the washing tank as described above, even when the range of the outer wall of the nozzle contaminated with the specimen is limited to the forward end portion of the nozzle, the amount of the washing solution supplied to the washing tank and the washing time are constant. For this reason, the washing solution and the washing time, which are uselessly consumed, are brought about.

The present disclosure has been made taking the foregoing problems into consideration, an object of which is to reduce the amount of consumption of a washing solution for a nozzle and the required time for washing.

Solution to Problem

One aspect of the present disclosure resides in a nozzle washing apparatus usable for collection of a specimen. The nozzle washing apparatus comprises a washing tank which accommodates a nozzle used to collect the specimen; a first discharge port which discharges a washing solution supplied into the washing tank from an upper portion of the washing tank; a second discharge port which discharges the washing solution supplied into the washing tank from a position lower than the first discharge port of the washing tank; a detector which detects a range of contact of an outer wall of the nozzle with the specimen; and a controller which discharges the washing solution supplied into the washing tank from one of the first discharge port and the second discharge port on the basis of a detection result obtained by the detector.

The nozzle washing apparatus may further comprise a first valve which opens/closes the first discharge port; and a second valve which opens/closes the second discharge port; wherein the controller can switch opening/closing of the first valve and/or the second valve on the basis of the detection result obtained by the detector.

Further, the detector can detect the range of contact of the outer wall of the nozzle with the specimen on the basis of at least one of an amount of the specimen and an amount of movement of the nozzle provided when the specimen is collected.

Further, the controller of the washing apparatus selects the second discharge port if the range of contact of the outer wall of the nozzle with the specimen is smaller than a predetermined range, or the controller selects the first discharge port if the range of contact is not smaller than the predetermined range.

Further, other aspects of the present disclosure include the disclosures of a dispensing apparatus and an analysis apparatus each comprising the nozzle washing apparatus described above as well as methods corresponding to the washing apparatus, the dispensing apparatus, and the analysis apparatus respectively.

Advantageous Effect

According to the present disclosure, it is possible to reduce the amount of consumption of the washing solution for the nozzle and the required time for washing.

DESCRIPTION OF THE EMBODIMENT

An explanation will be made below with reference to the drawings about an embodiment for carrying out the present disclosure. However, for example, the dimension or size, the material, the shape, and the relative arrangement of each of constitutive parts or components described in this embodiment are not intended to limit the scope of the disclosure only thereto unless specifically noted.

Embodiment

Figure 1:
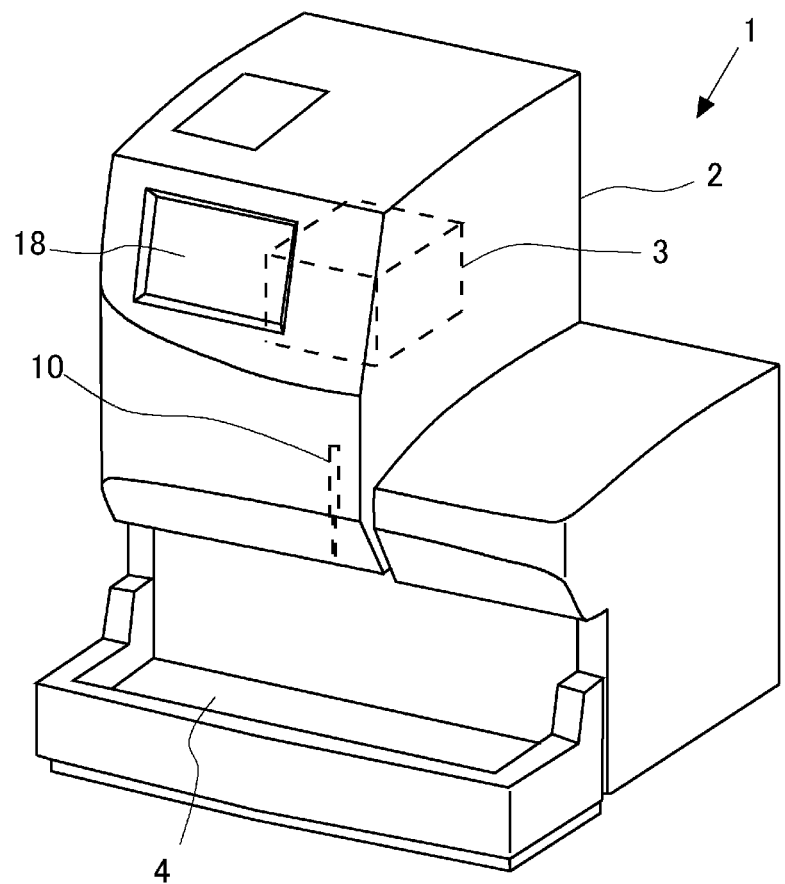
FIG. 1 shows a perspective view illustrating a schematic structure of an analysis apparatus concerning an embodiment.

FIG. 1 shows a perspective view illustrating a schematic structure of an analysis apparatus 1 concerning the embodiment. The analysis apparatus 1 is an apparatus to perform predetermined analysis for a specimen. The analysis apparatus 1 is provided with a control unit (controller) 3 which is accommodated in a casing 2, a placement unit 4, a nozzle 10, and a display unit 18. A container which accommodates the specimen (referred to as "specimen container") is placed on the placement unit 4. The nozzle 10 collects the specimen from the specimen container placed on the placement unit 4 by means of the suction, and the nozzle 10 drips (spots) the specimen onto a plurality of reagent pads installed on the test paper transported to the placement unit 4. Note that, urine, blood, and body fluid can be exemplified as the specimen. A urine collection cup or a test tube (including Spitz) can be exemplified for the specimen container. In this embodiment, an explanation will be made as exemplified by the urine analysis apparatus based on the use of the reagent pad. However, it is also allowable to use any other analysis apparatus.

For example, the absorption at a specified wavelength is measured by an optical system installed in the analysis apparatus 1 for the specimen spotted on the reagent pad. The inspection result, which is based on the measurement result, is outputted to the display unit 18.

Figure 2:
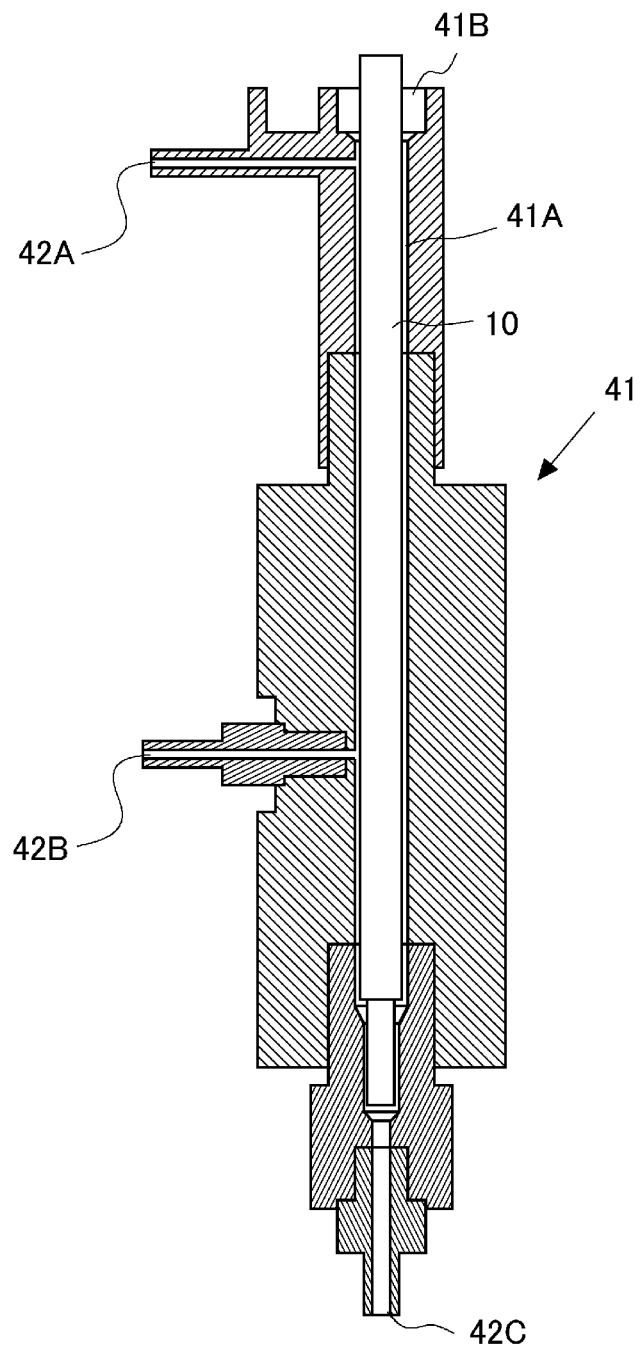
FIG. 2 shows a schematic structure of a washing tank of a nozzle washing apparatus.

When the spotting of the specimen on the reagent pad is terminated, the flow passage for the specimen including the interior of the nozzle 10 and the outer wall of the nozzle 10 are washed with a washing solution. On this account, the analysis apparatus 1 has a nozzle washing apparatus 20 (see FIG. 3). FIG. 2 shows a schematic structure of a washing tank 41 of the nozzle washing apparatus 20 (see FIG. 3). A storage unit 41A, which stores the washing solution, is formed for the washing tank 41. An opening 41B, which serves as an approaching port for the nozzle 10 when the nozzle 10 is accommodated, is provided for the storage unit 41A. Further, the washing tank 41 is provided with a first discharge port 42A, a second discharge port 42B, and a third discharge port 42C which are usable to discharge the washing solution from the storage unit 41A. The first discharge port 42A is provided at an upper portion of the washing tank 41. The third discharge port 42C is provided at a bottom portion of the washing tank 41. The second discharge port 42B is provided at a position lower than the first discharge port 42A, at an intermediate portion between the upper portion and the bottom portion of the washing tank 41. For example, in the case of the example shown in FIG. 2, the second discharge port 42B is provided at the position slightly lower than the center of the washing tank 41. Note that the second discharge port 42B may be provided at any position of the intermediate portion provided that the second discharge port 42B is disposed at the position lower than the first discharge port 42A. The third discharge port 42C is usable to discharge the washing solution which cannot be completely discharged from the first discharge port 42A and/or the second discharge port 42B and which remains in the washing tank 41.

Figure 3:
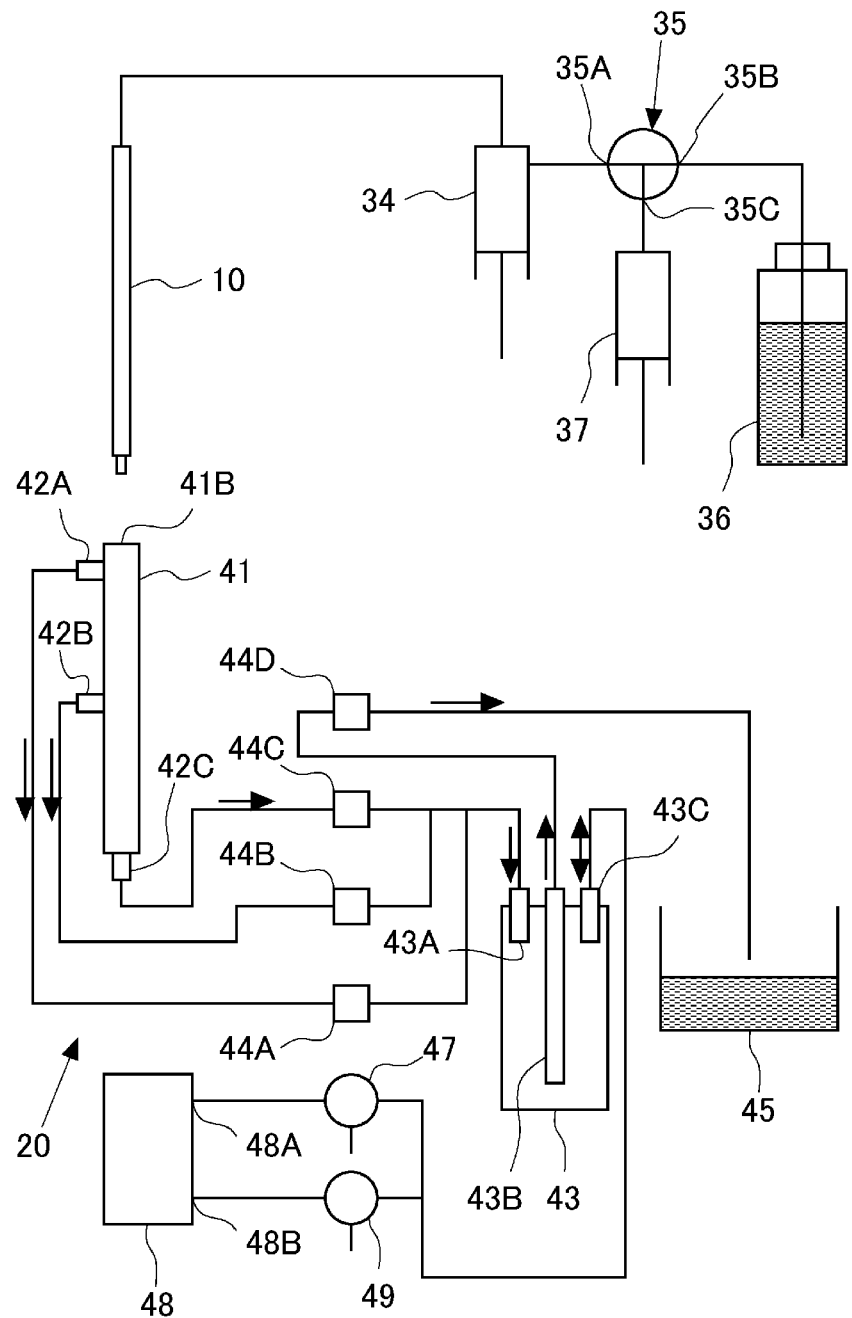
FIG. 3 shows a schematic arrangement of the washing apparatus of the analysis apparatus.

FIG. 3 shows a schematic arrangement of the nozzle washing apparatus 20 of the analysis apparatus 1. The nozzle 10 is connected to a spotting pump 34. The spotting pump 34 is connected to a first port 35A of a first changeover valve 35. The first changeover valve 35 is provided with a second port 35B and a common port 35C in addition to the first port 35A. The first changeover valve 35 makes communication between the common port 35C and any one port of the first port 35A and the second port 35B. The second port 35B of the first changeover valve 35 is connected to a washing solution bottle 36, and the common port 35C of the first changeover valve 35 is connected to a suction pump 37. The washing solution is stored in the washing solution bottle 36.

The first discharge port 42A of the washing tank 41 is connected to a first port 43A of a suction/discharge changeover bottle 43 via a first valve 44A. The second discharge port 42B of the washing tank 41 is connected to the first port 43A of the suction/discharge changeover bottle 43 via a second valve 44B. The third discharge port 42C of the washing tank 41 is connected to the first port 43A of the suction/discharge changeover bottle 43 via a third valve 44C. The first port 43A of the suction/discharge changeover bottle 43 is open at a relatively high position at the inside of the suction/discharge changeover bottle 43, wherein the liquid, which is stored in the suction/discharge changeover bottle 43, does not make any contact at the position.

Further, the suction/discharge changeover bottle 43 is provided with a second port 43B. The second port 43B of the suction/discharge changeover bottle 43 is connected to a waste liquid tank 45 via a fourth valve 44D. The second port 43B of the suction/discharge changeover bottle 43 is open at a relatively low position at the inside of the suction/discharge changeover bottle 43, wherein the second port 43B is open in the liquid stored in the suction/discharge changeover bottle 43.

Further, the suction/discharge changeover bottle 43 is provided with a third port 43C. The third port 43C of the suction/discharge changeover bottle 43 is connected to a suction port 48A of an air pump 43 via a second changeover valve 47. The third port 43C of the suction/discharge changeover bottle 43 is open at a relatively high position at the inside of the suction/discharge changeover bottle 43, wherein the liquid, which is stored in the suction/discharge changeover bottle 43, does not make any contact at the position.

The second changeover valve 47 makes communication between any one of the atmospheric air and the third port 43C of the suction/discharge changeover bottle 43 and a suction port 48 of the air pump 48. Further, the air pump 48 is provided with a discharge port 48B. The discharge port 48B of the air pump 48 is connected via a third changeover valve 49 to any one of the atmospheric air and the third port 48C of the suction/discharge changeover bottle 43. When the air pump 48 is operated, then the air is sucked from the suction port 48A, and the air is discharged from the discharge port 48B.

Figure 4:
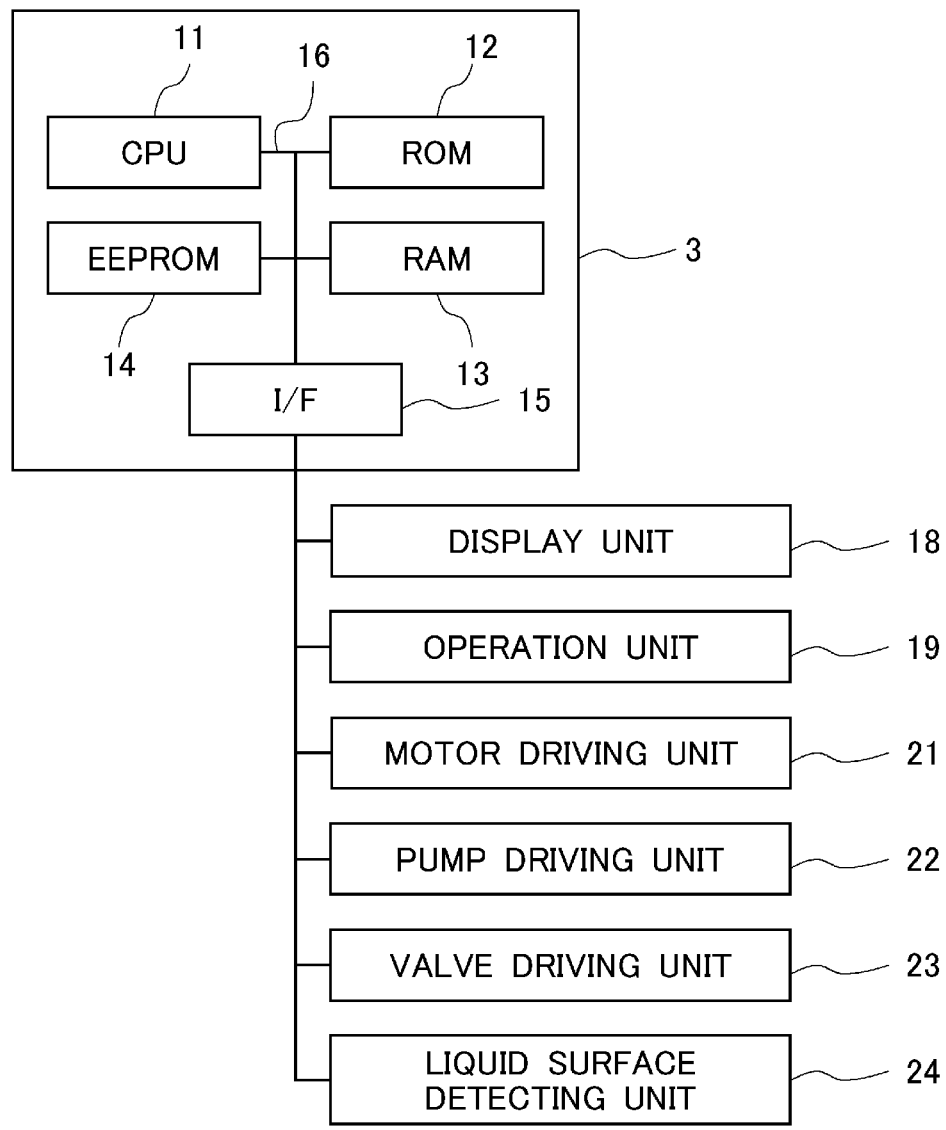
FIG. 4 shows a block diagram illustrating a control system concerning the embodiment.

FIG. 4 shows a block diagram illustrating a control system according to the embodiment of the present disclosure. The control unit 3 is provided with CPU 11, ROM 12, RAM 13, EEPROM 14, and an interface circuit 15 which are mutually connected to one another by a bus line 16. The display unit 18, an operation unit 19, a motor driving unit 21, a pump driving unit 22, a valve driving unit 23, and a liquid surface detecting unit 24 are connected to the interface circuit 15.

CPU (central processing unit) 11 is operated on the basis of a program which is stored in ROM (read only memory) 12 and which is read by RAM (random access memory) 13. CPU (central processing unit) 11 controls the entire analysis apparatus 1. The program and data for operating CPU 11 are stored in ROM 12. RAM 13 provides a work area for CPU 11, and RAM 13 temporarily stores various data and programs. EEPROM 14 stores, for example, various setting data. The interface circuit 15 controls the communication between CPU 11 and various circuits. The display unit 18 is provided with, for example, LCD (liquid crystal display) and a light emission diode. The display unit 18 is controlled by CPU 11 to display, for example, various information and inspection results. The operation unit 19 is provided with, for example, a key switch group, and the operation unit 19 supplies an operation signal to CPU 11 in accordance with the operation performed by a user.

The nozzle 10 is moved by the motor driving unit 21 in the horizontal direction and the upward-downward direction. The spotting pump 34, the suction pump 37, and the air pump 48 are driven by the pump driving unit 22. The first changeover valve 35, the second changeover valve 47, the third changeover valve 49, the first valve 44A, the second valve 44B, the third valve 44C, and the fourth valve 44D are driven by the valve driving unit 23. The liquid surface detecting unit 24 detects the height of the liquid surface in the specimen container. This will be described later on. The display unit 18, the operation unit 19, the motor driving unit 21, the pump driving unit 22, the valve driving unit 23, and the liquid surface detecting unit 24 are controlled by CPU 11 of the control unit 3.

Next, an explanation will be made about the operation to be performed when the specimen is sucked and when the nozzle 10 is washed. When the specimen is sucked, then the motor driving unit 21 is controlled by CPU 11, and the nozzle 10 is moved to a position disposed over or above the specimen container. After that, the nozzle 10 is moved downwardly into the specimen container. Then, the first changeover valve 35 is switched into a state in which the first port 35A and the common port 35C are communicated with each other, and the suction pump 37 is driven in the suction direction. Accordingly, the pressure in the suction pump 37 becomes a negative pressure, and the pressure in the spotting pump 34 becomes a negative pressure as well. In this way, when the pressure in the spotting pump 34 becomes the negative pressure, then the specimen is thereby sucked through the nozzle 10, and the specimen is supplied into the spotting pump 34.

Then, when the spotting is performed, then the motor driving unit 21 is controlled by CPU 11, and the nozzle 10 is moved to a position disposed over or above a reagent pad of the test paper. Further, the pump driving unit 22 is controlled by CPU 11. The spotting pump 34 is driven in the discharge direction, and the specimen is discharged from the spotting pump 34 to the nozzle 10. Then a predetermined amount of the specimen is spotted from the nozzle 10 onto the reagent pad. The operation as described above is repeated a number of times corresponding to the number of the reagent pads installed on the test paper, and the spotting step is terminated. The respective reagent pads, onto which the specimen has been spotted, are analyzed by means of known methods, and the analysis results are displayed on the display unit 18. Note that the steps described above are referred to by way of example in every sense. It is enough that the step of sucking the specimen from the specimen container by the nozzle 10 is included.

On the other hand, after the spotting is terminated, the washing of the nozzle 10 is performed. After the termination of the spotting, the motor driving unit 21 is controlled by CPU 11, and the nozzle 10 is moved to a position disposed over or above the washing tank 41. After that, the nozzle 10 is moved downwardly into the washing tank 41. Accordingly, the entire nozzle 10 is positioned at the inside of the washing tank 41. Then, the valve driving unit 23 is controlled by CPU 11, and the second port 35B of the first changeover valve 35 and the common port 35C of the first changeover valve 35 are communicated with each other. In this state, the pump driving unit 22 is controlled by CPU 11, and the suction pump 37 is driven in the suction direction. Accordingly, when a negative pressure is provided in the suction pump 37, a predetermined amount of the washing solution is sucked from the washing solution bottle 36 to the suction pump 37.

Subsequently, the valve driving unit 23 is controlled by CPU 11. The first port 35A of the first changeover valve 35 is communicated with the common port 35C of the first changeover valve 35. Further, the third valve 44C is opened, any one of the valves of the first valve 44A and the second valve 44B is opened, and the fourth valve 44D is closed. Further, the second changeover valve 47 makes communication between the suction port 48A of the air pump 48 and the third port 43C of the suction/discharge changeover bottle 43, and the third changeover valve 49 makes communication between the discharge port 48B of the air pump 48 and the atmospheric air. In this state, the pump driving unit 22 is controlled by CPU 11. The air pump 48 is driven, and the suction pump 37 is driven in the discharge direction. Accordingly, the washing solution, which is accommodated in the suction pump 37, passes through the flow passage for the specimen including the nozzle 10, and the washing solution is discharged from the nozzle 10 into the washing tank 41. In this situation, the interior of the suction/discharge changeover bottle 43 is sucked by the air pump 48. Therefore, the washing solution, which is discharged into the washing tank 41, is sucked into the suction/discharge changeover bottle 43 by means of the negative pressure. Further, a part of the washing solution, which is discharged from the nozzle 10 to the washing tank 41, washes the outer wall of the nozzle 10 during the period in which the part of the washing solution arrives at the first discharge port 42A or the second discharge port 42B from the forward end of the nozzle 10.

After that, the valve driving unit 23 is controlled by CPU 11. The fourth valve 44D is opened, and the first valve 44A, the second valve 44B, and the third valve 44C are closed. Further, the second changeover valve 47 makes communication between the suction port 48A of the air pump 48 and the atmospheric air, and the third changeover valve 49 makes communication between the discharge port 48B of the air pump 48 and the third port 43C of the suction/discharge changeover bottle 43. In this situation, the air pump 48 is driven. Therefore, the air is fed into the suction/discharge changeover bottle 43, and the interior of the suction/discharge changeover bottle 43 has a positive pressure. Accordingly, the washing solution, which is accommodated in the suction/discharge changeover bottle 43, is extruded from the second port 43B, and the washing solution is discharged as the waste liquid to the waste liquid tank 45. In this way, the interior and the outer wall of the nozzle 10 are washed with the washing solution.

Then, in the embodiment of the present disclosure, when the nozzle 10 is washed, the range, in which the outer wall of the nozzle 10 is washed, is changed depending on the range (hereinafter referred to as "contact range" as well) in which the outer wall of the nozzle 10 is brought in contact with the specimen when the specimen is collected. In this procedure, any one of the discharge ports of the first discharge port 42A and the second discharge port 42B is selected as the discharge port for discharging the washing solution by CPU 11. Then, if the first discharge port 42A is selected, then the first valve 44A is opened, and the second valve 44B is closed. On the other hand, if the second discharge port 42B is selected, then the first valve 44A is closed, and the second valve 44B is opened.

In this context, even if the nozzle 10 is moved downwardly into the specimen container by a fixed distance, the contact range of the nozzle 10 changes depending on the amount of the specimen accommodated in the specimen container (the amount may be also represented by the liquid surface height). That is, the smaller the amount of the specimen is (the lower the liquid surface of the specimen is), the smaller the contact range is, on condition that the distance, by which the nozzle 10 is moved downwardly toward the specimen container, is constant when the specimen is collected. In this way, the contact range changes depending on the height of the liquid surface of the specimen. On the other hand, the specimen disposed in the surface layer is collected in some cases, or the specimen disposed in the bottom layer is collected in other cased, depending on the contents of analysis. In such situations, the position (nozzle height), at which the nozzle 10 collects the specimen, is adjusted, and hence the distance of movement (distance of downward movement) of the nozzle 10 is changed. Therefore, even if the amount of the specimen accommodated in the specimen container is identical, the contact range of the nozzle 10 is changed. As described above, the contact range of the nozzle 10 can be sensed by detecting the amount of the specimen and/or the distance of movement of the nozzle when the specimen is collected.

If the upper end portion of the contact range of the nozzle 10 is disposed at a position lower than the second discharge port 42B in a state in which the nozzle 10 is arranged at the position for the washing in the washing tank 41, then the entire contact range can be washed, even if the washing solution is discharged from the second discharge port 42B. If the upper end portion of the contact range is lower than the second discharge port 42B, and it is unnecessary to wash a part of the outer wall of the nozzle 10 corresponding to the range ranging from the second discharge port 42B to the first discharge port 42A, then the discharge of the washing solution from the first discharge port 42A causes the waste of the washing solution. Further, the time, which is required until the liquid surface of the washing solution arrives at the first discharge port 42A, is longer than the time which is required until the liquid surface of the washing solution discharged (supplied) from the nozzle 10 arrives at the second discharge port 42B. Therefore, if the washing solution is discharged from the first discharge port 42A, the washing time is prolonged as compared with if the second discharge port 42B is used.

In the embodiment of the present disclosure, the height of the liquid surface of the specimen accommodated in the specimen container is detected, and the contact range is calculated on the basis of an obtained detection value. Then, when the nozzle 10 is arranged at the washing position in the washing tank 41, if the contact range of the nozzle 10 is not more than a predetermined range, then the washing solution is discharged from the second discharge port 42B. If the contact range of the nozzle 10 is larger than the predetermined range, the washing solution is discharged from the first discharge port 42A. The predetermined range is the range from the forward end of the nozzle 10, and the predetermined range is the range in which the washing can be performed when the washing solution is discharged from the second discharge port 42B. In this way, it is determined from which discharge port the washing solution is discharged, and the valve connected to the discharge port is controlled, on the basis of the detection result of the contact range. Note that if the upper end portion of the contact range of the nozzle 10 does not arrive at the second discharge port 42B (i.e., if the contact range is only the range which is lower than the second discharge port 42B), the entire contact range can be washed, even when the washing solution is discharged from the second discharge port 42B. Therefore, it is affirmed that the contact range of the nozzle 10 is not more than the predetermined range. On the other hand, if the contact range of the nozzle 10 arrives at the second discharge port 42B (i.e., if the contact range includes the range higher than the second discharge port 42B), a part of the contact range cannot be washed, even when the washing solution is discharged from the second discharge port 42B. Therefore, it is affirmed that the contact range of the nozzle 10 is larger than the predetermined range.

The liquid surface height of the specimen accommodated in the specimen container is detected by the liquid surface detecting unit 24. Then, the liquid surface height can be detected as follows. Note that the liquid surface height of the specimen is detected in conformity with the timing of the suction of the specimen from the specimen container. For example, the nozzle 10 and the casing 2 are regarded as electrodes. The liquid surface height of the specimen can be detected by sensing the amount of change of the electrostatic capacity C of a capacitor constructed by the dielectric constant between the nozzle 10 and the casing 2.

If the specimen is contained in the specimen container when the nozzle 10 is moved downwardly into the specimen container, the electrostatic capacity C changes if the nozzle 10 is brought in contact with the specimen. The liquid surface height of the specimen can be calculated from the amount of change and the positional relationship between the specimen container and the nozzle 10. The position of the nozzle 10 may be detected by a sensor. Alternatively, the position of the nozzle 10 may be estimated on the basis of the supplied electric power and/or the operation time of the actuator. Note that it is also possible to judge whether or not the washing solution is discharged from the second discharge port 42B without calculating the liquid surface height. For example, if the amount of downward movement of the nozzle 10 from the position of the change of the electrostatic capacity is less than a threshold value, it is possible to judge that the upper end portion of the contact range of the nozzle 10 is disposed at a position lower than the second discharge port 42B. Therefore, it is appropriate to discharge the washing solution from the second discharge port 42B. If the amount of downward movement of the nozzle 10 from the position of the change of the electrostatic capacity is not less than the threshold value, it is possible to judge that the upper end portion of the contact range of the nozzle 10 is disposed at a position higher than the second discharge port 42B. Therefore, it is appropriate to discharge the washing solution from the first discharge port 42A.

Further, in addition to the nozzle 10, a metal pipe, which has a length approximately equivalent to the length of the nozzle 10, is moved downwardly into the specimen container together with the nozzle 10, and a voltage is applied beforehand between the nozzle 10 and the metal pipe. The liquid surface height of the specimen can be calculated on the basis of a conduction state between the nozzle 10 and the metal pipe provided in this situation.

Figure 5:
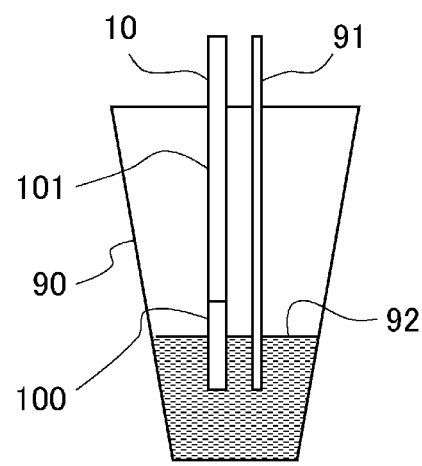
FIG. 5 shows an example to determine a liquid surface height of a specimen.
Figure 6:
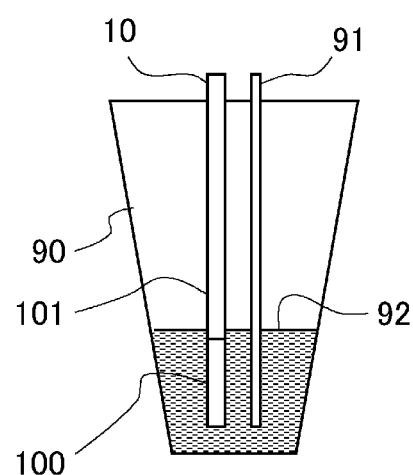
FIG. 6 shows an example to determine a liquid surface height of a specimen.

FIGS. 5 and 6 show examples to determine the liquid surface height of the specimen. As shown in FIGS. 5 and 6, a metal pipe 91 is provided in parallel to the nozzle 10. The nozzle 10 and the metal pipe 91 are moved downwardly into the specimen container 90 in a synchronized manner. A material, through which the current flows and which is not corroded by the specimen, is used for the metal pipe 91. Note that the nozzle 10 shown in FIGS. 5 and 6 is provided with a forward end portion 100 which is an insulator and a main body portion 101 which is a conductor (for example, made of metal). In a state shown in FIG. 5, the main body portion 101 of the nozzle 10 does not arrive at the liquid surface 92. Therefore, even if the voltage is applied between the nozzle 10 and the metal pipe 91, little current flows. On the other hand, in a state shown in FIG. 6, the current flows if the voltage is applied between the nozzle 10 and the metal pipe. It is possible to calculate the liquid surface height of the specimen from the positional relationship between the specimen container 90 and the nozzle 10 provided when the conduction state changes. The control unit 3 calculates the contact range from the liquid surface height of the specimen as described above, and thus the control unit 3 functions as the detector according to the present disclosure.

Note that in the case of the nozzle 10 shown in FIGS. 5 and 6, it is also possible to judge whether or not the washing solution is to be discharged from the second discharge port 42B without calculating the liquid surface height. For example, when the length of the forward end portion 100 is conformed to the height of the second discharge port 42B beforehand, if the conduction is detected upon the collection of the specimen, then it is possible to judge that the contact range of the nozzle 10 is disposed at a position higher than the second discharge port 42B. Therefore, it is appropriate that the washing solution is discharged from the first discharge port 42A. On the other hand, if the conduction is not detected, it is possible to judge that the contact range of the nozzle 10 is disposed at a position lower than the second discharge port 42B. Therefore, it is appropriate that the washing solution is discharged from the second discharge port 42B.

Figure 7:
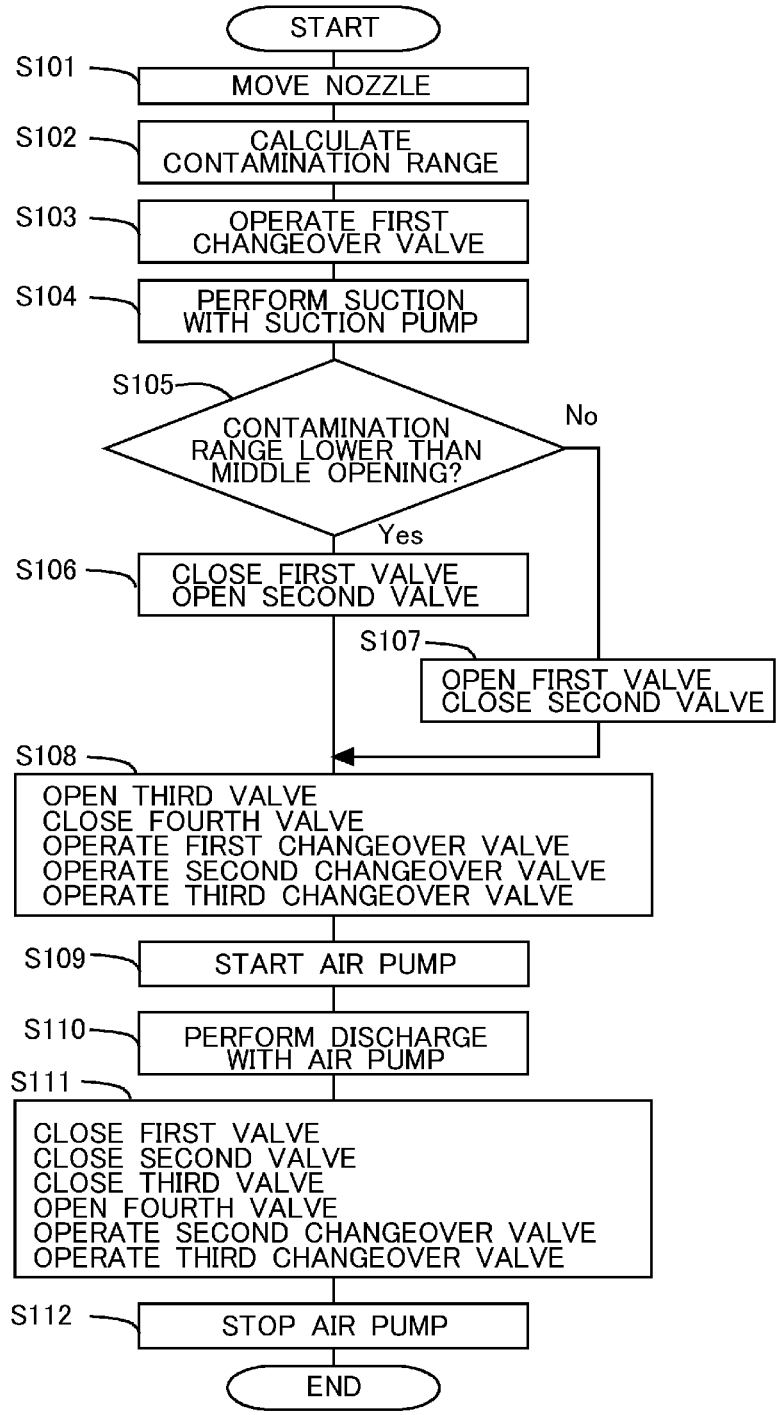
FIG. 7 shows a flow chart illustrating a flow of nozzle washing concerning the embodiment.

FIG. 7 shows a flow chart illustrating a flow of the washing of the nozzle 10 according to the embodiment of the present disclosure. This flow chart is executed by the control unit 3 after the termination of the collection of the specimen, i.e., when it is necessary to wash the nozzle 10.

In Step S101, the nozzle 10 is moved into the washing tank 41. If the movement of the nozzle 10 is terminated, the routine proceeds to Step S102.

In Step S102, the contact range is calculated. The liquid surface height of the specimen in the specimen container and the downward movement distance of the nozzle 10 from the liquid surface height are calculated by means of the method described above when the specimen is sucked from the specimen container, and the liquid surface height and the downward movement distance are stored in RAM 13. The downward movement distance of the nozzle 10 from the liquid surface height corresponds to the distance of the contact range from the forward end of the nozzle 10. If the contact range is acquired, the routine proceeds to Step S103.

In Step S103, the first changeover valve 35 is operated, and the second port 35B of the first changeover valve 35 and the common port 35C of the first changeover valve 35 are communicated with each other. If the operation of the first changeover valve 35 is terminated, the routine proceeds to Step S104.

In Step S104, the suction pump 37 is driven in the suction direction. Accordingly, a predetermined amount of the washing solution is sucked from the washing solution bottle 36 to the suction pump 37. Note that the predetermined amount may be changed depending on the contact range. That is, it is also allowable that the wider the contact range is, the larger the predetermined amount is. After the predetermined amount of the washing solution is sucked into the suction pump 37, the routine proceeds to Step S105.

In Step S105, it is judged whether or not the contact range of the nozzle 10 exists within a range lower than the second discharge port 42B only. That is, it is judged whether or not the entire contact range of the nozzle 10 can be washed even if the washing solution is discharged from the second discharge port 42B. Note that in the embodiment of the present disclosure, an allowance or margin may be provided such that the washing solution may be discharged from the second discharge port 42B if the contact range of the nozzle 10 is lower than the second discharge port 42B by a predetermined distance. If the affirmative judgment is made in Step S105, the routine proceeds to Step S106. On the other hand, if the negative judgment is made, the routine proceeds to Step S107.

In Step S106, the first valve 44A is closed, and the second valve 44B is opened. That is, in order to discharge the washing solution from the second discharge port 42B, the second discharge port 42B and the suction/discharge changeover bottle 43 are communicated with each other. If the process of Step S106 is terminated, the routine proceeds to Step S108.

On the other hand, in Step S107, the first valve 44A is opened, and the second valve 44B is closed. That is, in order to discharge the washing solution from the first discharge port 42A, the first discharge port 42A and the suction/discharge changeover bottle 43 are communicated with each other. If the process of Step S107 is terminated, the routine proceeds to Step S108.

In Step S108, the third valve 44C is opened, and the fourth valve 44D is closed. The first changeover valve 35 is operated, and thus the first port 35A of the first changeover valve 35 and the common port 35C of the first changeover valve 35 are communicated with each other. The second changeover valve is operated, and thus the suction port 48A of the air pump 48 and the third port 43C of the suction/discharge changeover bottle 43 are communicated with each other. The third changeover valve 49 is operated, and thus the discharge port 48B of the air pump 48 and the atmospheric air are communicated with each other. That is, such a state is provided that the washing solution can flow through the interior and the outer wall of the nozzle 10. If the process of Step S108 is terminated, the routine proceeds to Step S109.

In Step S109, the air pump 48 is driven. If the air pump 48 is driven, then the routine proceeds to Step S110, and the suction pump 37 is driven in the discharge direction. In this way, the air pump 48 and the suction pump 37 are driven, and thus the washing solution, which is accommodated at the inside of the suction pump 37, passes through the flow passage for the specimen including the nozzle 10. The washing solution is discharged from the nozzle 10 into the washing tank 41. Further, the washing solution, which is discharged into the washing tank 41, is sucked into the suction/discharge changeover bottle 43. In this procedure, the contact range of the nozzle 10 is washed. If the washing of the nozzle 10 is completed, the routine proceeds to Step S111.

In Step S111, the first valve 44A, the second valve 44B, and the third valve 44C are closed, and the fourth valve 44D is opened. The second changeover valve 47 is operated, and the suction port 48A of the air pump 48 and the atmospheric air are communicated with each other. The third changeover valve 49 is operated, and the discharge port 48B of the air pump 48 and the third port 43C of the suction/discharge changeover bottle 43 are communicated with each other. Accordingly, such a state is provided that the waste liquid can be discharged to the waste liquid tank 45. After accommodating all of the waste liquid in the waste liquid tank 45, the routine proceeds to Step S112, and the air pump 48 is stopped. In this way, the interior and the outer wall of the nozzle 10 are washed with the washing solution.

As explained above, according to the embodiment of the present disclosure, the range of the washing is adjusted depending on the contact range of the nozzle 10. Therefore, it is possible to realize the saving of the washing solution and the shortening of the washing time.

Note that in the embodiment of the present disclosure, only one second discharge port 42B is provided between the first discharge port 42A and the third discharge port 42C of the washing tank 41. However, in place thereof, it is also allowable to provide two or more second discharge ports 42B. Then, the contact range of the nozzle 10 may be detected, and the washing solution may be discharged by selecting the second discharge port 42B which exists at the lowest position, of the second discharge ports 42B capable of washing the entire contact range.

Further, in the embodiment of the present disclosure, the second discharge port 42B is provided in the vicinity of the center of the washing tank 41. However, there is no limitation thereto. The second discharge port 42B may be provided at another position. For example, if the contact range can be predicted, the second discharge port 42B may be provided at a position at which the predictable contact range can be washed.

Further, in the embodiment of the present disclosure, the explanation has been made as exemplified by the nozzle washing apparatus 20 shown in FIG. 3 by way of example. However, the method for discharging the washing solution is not limited thereto. For example, it is also allowable to adopt such a structure that the washing solution is discharged from the washing tank 41 without using the suction/discharge changeover bottle 43 and the air pump 48.

The invention claimed is:

1. A nozzle washing apparatus comprising:
   a washing tank which accommodates a nozzle used to collect a specimen;
   a first discharge port positioned at an upper portion of the washing tank, wherein the first discharge port is configured to discharge washing solution out of the washing tank;
   a first valve which can open and close the first discharge port;
   a second discharge port positioned on the washing tank lower than the first discharge port, wherein the second discharge port is configured to discharge washing solution out of the washing tank;
   a second valve which can open and close the second discharge port;
   a detector for detecting a range of contact of an outer wall of the nozzle with the specimen;
   a controller configured to control opening and closing of the first discharge port and the second discharge port by controlling the opening and closing of the first and second valves; and
   wherein the controller communicates with the detector such that, based on the detected range of contact of the outer wall with the specimen, the controller is configured to selectively open or close each of the first and second valves in the following manner:
   when the detected range of contact is at or above a predetermined threshold, the second valve is closed and the first valve is opened; and
   when the detected range of contact is below the predetermined threshold, the first valve is closed and the second valve is opened.

2. The nozzle washing apparatus according to claim 1, wherein the detector is further configured to detect the range of contact of the outer wall of the nozzle with the specimen on the basis of at least one of an amount of the specimen and an amount of movement of the nozzle when the specimen is collected.

3. A dispensing apparatus comprising a nozzle and the nozzle washing apparatus of claim 1.

* * * * *